United States Patent
Zhou

(10) Patent No.: US 10,548,940 B2
(45) Date of Patent: Feb. 4, 2020

(54) PHARMACEUTICAL COMPOSITION FOR CONTROLLING BLOOD LIPIDS AND BODY WEIGHT, AND USE THEREOF

(71) Applicants: BEIJING HEBABIZ MANAGEMENT CO., LTD, Beijing (CN); James Zhou, Beijing (CN)

(72) Inventor: James Zhou, Beijing (CN)

(73) Assignee: BEIJING HEBABIZ BIOTECHNOLOGY CO., Inc., Beijing (CN)

( * ) Notice: Subject to any disclaimer, the term of this patent is extended or adjusted under 35 U.S.C. 154(b) by 0 days.

(21) Appl. No.: 15/310,897

(22) PCT Filed: Nov. 4, 2014

(86) PCT No.: PCT/CN2014/000968
§ 371 (c)(1),
(2) Date: Nov. 14, 2016

(87) PCT Pub. No.: WO2015/172273
PCT Pub. Date: Nov. 19, 2015

(65) Prior Publication Data
US 2017/0080043 A1 Mar. 23, 2017

(30) Foreign Application Priority Data

May 12, 2014 (CN) .......................... 2014 1 0197015

(51) Int. Cl.
| | | |
|---|---|---|
| A61K 36/00 | (2006.01) | |
| A61K 36/9066 | (2006.01) | |
| A61K 36/076 | (2006.01) | |
| A61K 36/484 | (2006.01) | |
| A61K 36/537 | (2006.01) | |
| A61K 36/54 | (2006.01) | |
| A61K 36/718 | (2006.01) | |
| A61K 36/736 | (2006.01) | |
| A61K 36/65 | (2006.01) | |

(52) U.S. Cl.
CPC ........ *A61K 36/9066* (2013.01); *A61K 36/076* (2013.01); *A61K 36/484* (2013.01); *A61K 36/537* (2013.01); *A61K 36/54* (2013.01); *A61K 36/65* (2013.01); *A61K 36/718* (2013.01); *A61K 36/736* (2013.01); *A61K 2236/15* (2013.01); *A61K 2236/331* (2013.01); *A61K 2236/37* (2013.01); *A61K 2236/51* (2013.01)

(58) Field of Classification Search
CPC .................................................... A61K 36/00
See application file for complete search history.

(56) References Cited

FOREIGN PATENT DOCUMENTS

| | | | |
|---|---|---|---|
| CN | 1296070 | A | 5/2001 |
| CN | 1651056 | A | 8/2005 |
| CN | 1660309 | A | 8/2005 |
| CN | 1748738 | A | 3/2006 |
| CN | 1985913 | A | 6/2007 |
| CN | 101214352 | A | 7/2008 |
| CN | 101310739 | A | 11/2008 |
| CN | 101491606 | A | 7/2009 |
| CN | 101564442 | A | 10/2009 |
| CN | 101757562 | A * | 6/2010 |
| CN | 101757562 | A * | 6/2010 |
| CN | 102085257 | A | 6/2011 |
| CN | 102188560 | A | 9/2011 |
| CN | 102240372 | A | 11/2011 |
| CN | 102772517 | A | 11/2012 |
| CN | 102846760 | A | 1/2013 |
| CN | 102908599 | A | 2/2013 |
| JP | 2002114695 | A | 4/2002 |
| JP | 2005206589 | A | 8/2005 |
| JP | 2008133272 | A | 6/2008 |
| JP | 2009114179 | A | 5/2009 |
| JP | 2010227033 | A | 10/2010 |

OTHER PUBLICATIONS

Park, Tumor initiation inhibition through inhibition COX-1 activity of a traditional Korean herbal prescription, Geiji-Bokryung-Hwan, in human hepatocarcinoma cells. Immunopharmacology and immunotoxicology, (2005) vol. 27, No. 3, pp. 473-483 (Year: 2005).*

Fujimoto et al., "Evidence-Based Efficacy of Kampo Formulas in a Model of Non Alcoholic Fatty Liver", Department of Japanese Oriental Medicine, (2007), pp. 328-337.

Nakagawa et al., "Keishibukuryogan ameliorates glucose intolerance and hyperlipidemia in Otsuka Long-Evans Tokushima Fatty (OLETF) rats", Diabetes Research and Clinical Practice, 80, (2008) pp. 40-47.

(Continued)

*Primary Examiner* — Qiuwen Mi

(74) *Attorney, Agent, or Firm* — Bachman & LaPointe, PC

(57) ABSTRACT

The invention provides a traditional Chinese medicine composition for the control of blood lipids and/or weight of body, which includes Poria and Paeoniae Radix Alba, etc. the traditional Chinese medicine composition can be applied in reducing the total cholesterol level, triacylglycerol level, and low density lipoprotein cholesterol level in the body; increasing body high density lipoprotein cholesterol level, reducing uric acid level, and/or reducing symptoms of fatty liver. The invention also provides preparation methods and applications of this traditional Chinese medicine composition.

11 Claims, No Drawings

(56) References Cited

OTHER PUBLICATIONS

German office action for patent application No. 11 2014 006 651.6 dated Feb. 2, 2018.
Nakagawa et al., "Keishibukuryogan ameliorates glucose intolerance and hyperlipidemia in Otsuka Long-Evans Tokushima Fatty (OLETF) rats", Diabetes Research & Clinical Practice, vol. 80, pp. 40-47, (2008).
Nakagawa et al., "Therapeutic usefulness of Keishi-bukuryo-gan for diabetic nephropathy", Journal of Pharmacy and Pharmacology, vol. 55, pp. 219-227, (2003).
Wang et al., Journal of Changchum College of Traditional Chinese Medicine, vol. 13, pp. 14, (1997).
Fujimoto et al., Abstract of the 37th Lectures in the Liver Institute of Japan entitled "Liver", in Supplement, vol. 48, p. A556 (0-78), (2007).
Dictionary of Traditional Chinese Medicines, vol. 3, pp. 1729-1733, Shogakukan, (1998).
Japanese office action for patent application No. 2017-512078 dated Jun. 5, 2018.
Chinese office action for patent application No. 2017-512078 dated Jun. 5, 2018.
Japanese office action for patent application No. 2017-512078 dated Feb. 13, 2019.

* cited by examiner

PHARMACEUTICAL COMPOSITION FOR CONTROLLING BLOOD LIPIDS AND BODY WEIGHT, AND USE THEREOF

FIELD OF TECHNOLOGY

The invention belongs to the field of traditional medicine. Specifically, the invention relates to a traditional Chinese medicine composition and its preparation, it adds and subtracts the categories of the crude drug of Guizhi Fuling pill, which is especially suitable for control of blood fat and weight of human body.

BACKGROUND TECHNOLOGY

Guizhi Fuling pill is a traditional Chinese traditional compound patent medicine, originated from "Golden Chamber Synopsis", it is made by the same amount of Cinnamomi Ramulus, Poria, Moutan Cortex, Paeoniae Radix Rubra, and Persicae Semen after crushing and honey refining, and it is mainly used for gynecological diseases, including for women in places with blood stasis, amenorrhea, abdominal pain, or postpartum lochia (see SFDA standard WS-11424 (ZD-1424)-2002, etc.).

In recent years, the research on Guizhi Fuling pill is basically limited to the improvement of its preparation and the corresponding preparation method. For example, Chinese patent application No. 201210260676 discloses a preparation method of Guizhi Fuling pill, including preparation of powder, pill of Guizhi Fuling pill, the first microwave vacuum drying, coating and the secondary microwave vacuum drying;

Chinese patent application No. 201110005242 discloses a preparation method of Cinnamomi Ramulus Poria pellets, including grounding Poria into fine powder, extracting the volatile oil of Cinnamomi Ramulus, distilling and crystallizing the water extract of Moutan Cortex, mixing Paeoniae Radix Rubra and boiling Persicae Semen, adding ethanol and inclusion of cyclodextrin, processing extract and obtaining the mold core, combining the adhesive and preparing mold pellet, finally spraying, coating, and obtaining the pellet;

Chinese patent application number 200810105202 discloses a Cinnamomi Ramulus Poria preparation and its preparation method, wherein; it applies the vibration type ultra-fine pulverization technology and improves the utilization rate of the medicinal materials;

Chinese patent application No. 200810150311 discloses a Cinnamomi Ramulus Poria preparation and its preparation method, which use supercritical carbon dioxide mixed extraction technology, are made into soft capsules or tablets, hard capsules, granules, mixture and other dosage forms;

Chinese patent application No. 2005100608144th discloses a Cinnamomi Ramulus Poria drop pill. Its preparation processes include distilling the Moutan Cortex with water vapor, collecting distilled liquid, separating and obtaining the volatile components, performing refluxing extraction to dregs and Cinnamomi Ramulus, Persicae Semen, Paeoniae Radix Rubra or Paeoniae Radix Alba and Poria by ethyl alcohol, recovering alcohol until non-alcohol taste, concentrating to paste, adding water and decocting the dregs, filtering, and combining filtrating liquid, reducing pressure and concentrating to clear paste, and combining the paste above mentioned, mixing with the remaining Poria fine powder, drying, crushing, performing 100 mesh sieve, adding the volatile components above, obtaining the main drug extracts; heating the excipient at 60-105° C. and making it into the melt and mixing it with the main drug extract, dripping it at 70-100° C., dripping it to the methyl silicone oil or vegetable oil or liquid paraffin coolant with temperature of 5~30° C. for cooling, remove Coolant, the pill will be obtained after selection;

Chinese patent application No. 200410100866 discloses Cinnamomi Ramulus Poria soft capsule and its preparation process; wherein it basically consists of water or alcohol extract of Cinnamomi Ramulus, Poria, Moutan Cortex, Paeoniae Radix Rubra, Persicae Semen, diluent, suspending agent and wetting agent; capsule material is made from gelatin, plasticizer and water; it is used for treatment of dysmenorrhea, habitual abortion, asthma and other diseases;

Chinese patent application No. 2004100691155th discloses a Cinnamomi Ramulus Poria orally disintegrating tablets and its preparation method, which are composed of effective components extracted Cinnamomi Ramulus, Poria Moutan Cortex, Paeoniae Radix Rubra, Persicae Semen and medicinal excipient. The medicinal excipient includes erythritol and chitin or low substituted hydroxypropyl methylcellulose or carboxymethyl sodium carboxymethyl starch or cross-linked carboxymethyl starch sodium or insoluble cross-linked polyvinylpyrrolidone.

The inventor found that these studies or records of the Guizhi Fuling pill were basically limited to gynecological diseases, not involving the control of body weight and blood lipid, especially the study of existing technology not only didn't study these effects in depth, but also made the preparation process more complicated; for the treatment effect, especially the control of human blood lipid effect, it had no improvement.

In addition, some Chinese herbal compounds also include Ramulus, cinnamomi, Poria, Moutan Cortex, Paeoniae Radix Rubra and other crude drug, but they selects ten tastes of raw materials (crude drug), even select dozens tastes of raw materials (crude drug), the formula is very complicated and the production quality is difficult to control.

SUMMARY OF THE INVENTION AND DETAILED DESCRIPTION

After long and hard study, with some luck, the inventor unexpectedly found that added and simplified the crude drug of Guizhi, Fuling pill and made the new traditional Chinese medicine composition (formula). Surprisingly, the traditional Chinese medicine composition (formula) can significantly improve the efficacy of the control of human body blood lipid. In addition, the preparation process of the traditional Chinese medicine composition can be used in the conventional process step by step, without the addition of new production equipment, and has the advantages of simple steps, easy operation and monitoring, further reduce the cost.

The objective of the invention is to provide a new method for treatment of high blood cholesterol, obesity, accordingly, to provide a new traditional Chinese medicine composition, whose crude drug includes Poria and Paeoniae Radix Rubra, used to control the body fat and weight. Compared with Guizhi Fuling pill, the traditional Chinese medicine composition of the invention is a more effective and better formula preferably used in control of body blood lipid and body weight. In addition, the invention also provides a preparation method of the composition, its drug preparation and application.

Specifically, in the first aspect, the present invention provides a Chinese traditional medicine composition for controlling blood lipid and/or body weight which is made from Poria, Paeoniae Radix Rubra and any of the following crude drug:
  Group A: Moutan Cortex and Cinnamomi Ramulus;
  Group B: Moutan Cortex, Cinnamomi Ramulus, Persicae Semen and radix et rhizoma glycyrrhizae; and,
  Group C: Salviae miltiorrhizae Radix et Rhizoma, Curcumae longae Rhizoma and Coptidis Rhizoma.

In other words, the traditional Chinese medicine composition in the first aspect of the invention may be made from Poria, Paeoniae Radix Rubra, Moutan Cortex and Cinnamomi Ramulus, or also be made from Poria, Paeoniae Radix Rubra, Moutan Cortex, Cinnamomi Ramulus, Persicae Semen and radix et rhizoma glycyrrhizae, or also made from Poria, Paeoniae Radix Rubra, Salviae miltiorrhizae Radix et Rhizoma, Curcumae longae Rhizoma and Coptidis Rhizoma.

In this paper, crude drug, that is the raw material of Chinese traditional medicine, all are known by the technical personnel of traditional Chinese medicine field, and can also be purchased through the medicine market. In this paper, the vast majority of Chinese medicine are used their scientific names, such as Poria, Cinnamomi Ramulus, Persicae Semen, radix et rhizoma glycyrrhizae, Salviae miltiorrhizae Radix et Rhizoma, Curcumae longae Rhizoma and rhizoma coptidi. In this paper, or otherwise without opposite instructions, Especially in the concrete implementation method, *Paeonia lactiflora* prefers Paeoniae Radix Rubra; Moutan Cortex refers to Moutan Cortex.

Preferentially, in the traditional Chinese medicine composition in the first aspect of the invention, the weight proportion of every crude drug is as following:
Poria for 3 parts approximately, Paeoniae Radix Rubra for 3 parts approximately, Moutan Cortex for 3 parts approximately, Cinnamomi Ramulus for 3 parts approximately, Persicae Semen for 3 parts approximately, and radix et rhizoma glycyrrhizae for 2 parts approximately, Salviae miltiorrhizae Radix et Rhizoma for 3 parts approximately, Curcumae longae Rhizoma for 3 parts approximately, Coptidis Rhizoma for 1.2 parts approximately.

That is to say, the traditional Chinese medicine composition in the first aspect of the invention may preferentially be made from Poria for 3 parts approximately, Paeoniae Radix Rubra for 3 parts approximately, Moutan Cortex for 3 parts approximately, Cinnamomi Ramulus for 3 parts approximately, or may preferentially be made from Poria for 3 parts approximately, Paeoniae Radix Rubra for 3 parts approximately, Moutan Cortex for 3 parts approximately, Cinnamomi Ramulus for 3 parts approximately, Persicae Semen for 3 parts approximately, and radix et rhizoma glycyrrhizae for 2 parts approximately, or may preferentially be made from Poria for 3 parts approximately, Paeoniae Radix Rubra for 3 parts approximately, Salviae miltiorrhizae Radix et Rhizoma, for 3 parts of approximately, Curcumae longae Rhizoma for 3 parts approximately, and Coptidis Rhizoma for 1.2 parts approximately.

In this paper, for the sake of clarity, the term "approximately" refers to the scope of the numerical value +10% in modification. For example, approximate 3 refers to 2.7~3.3, approximate 2 refers to 1.8~2.2, approximate 1.2 is preferably 1.08~1.32., preferably "approximate" in the scope of the modified value refers to the value of +5%, more preferably that refers to the range of the value of +3% or +2% or +1%.

Preferably in the traditional Chinese medicine composition in the first aspect of the invention, the process of the preparation includes adding water and/or alcohol decocting, including water decocting, alcohol decocting, aqueous solution with added alcohol (such as aqueous solution with 30~70% (V/V) alcohol) decocting. The preferably alcohol is ethanol.

In the traditional Chinese medicine composition of the first aspect of the invention, crude drug includes many volatile components, so it can be boiling in a closed container, so as to prevent the loss of these components, which is clearly required in a lot of existing technologies. However, the inventors have found that, at least for the inventor concerned control of body weight and blood lipid and/or indications, the composition with loss of these volatile efficacy component can still achieve excellent curative effect, so in the optimized traditional Chinese medicine composition in the first aspect of the invention, the preparation process includes adding water and decocting in an open container. It can use low cost and high safety decocting equipment.

More referentially in the optimized traditional Chinese medicine composition in the first aspect of the present invention, the preparation process includes:
(1) crush and mix the crude drug, then obtain the mixed powder of crude drug;
(2) Add water into and soak the mixed powder of crude drug obtained in step (1) (preferentially soaking for 0.5~2 hours), then decoct in an open container (preferentially decoction for 0.5~2 hours), and obtain the decocted liquid;
(3) Filter the decocted liquid obtained in step (2), and obtain the medicine liquid; and,
(4) Choose and dry (preferred freeze drying) any of the medicine liquid obtained in step (3).

The traditional Chinese medicine composition in the first aspect can be applied in reducing the total cholesterol level, triacylglycerol level, and low density lipoprotein cholesterol level in the body; increasing body high density lipoprotein cholesterol level, reducing uric acid level, and/or reducing symptoms of fatty liver. The traditional Chinese medicine compositions in different recipes have different improvement effect in total cholesterol level, triacylglycerol level, low density lipoprotein cholesterol level, high density lipoprotein cholesterol level, uric acid level, and/or fatty liver; therefore, it is easier to use these compositions for therapy. For example, when the total cholesterol level is normal and some other indicators are abnormal, the preparation ZL004 is particularly suitable; and as for triacylglycerol level is normal, and other indicators are abnormal, the preparation ZL051 is particularly suitable.

In the second aspect, the invention provides a preparation method of the Chinese medicine composition traditional involved in the first aspect of the invention:
(1) crush and mix the crude drug, then obtain the mixed powder of crude drug;
(2) Add water into and soak the mixed powder of crude drug obtained in step (1) (preferentially soaking for 0.5-2 hours), then perform decoction in an open container (preferentially decoction for 0.5~2 hours), and obtain the decocted liquid;
(3) Filter the decocted liquid obtained in step (2), and obtain the medicine liquid; and,
(4) Choose and dry (preferred freeze drying) any of the medicine liquid obtained in step (3).

If there is no contradiction, the second aspects of the optimization scheme of the invention can refer to the corresponding optimization scheme in the first aspect of the invention. For example, in the preparation method of the second aspects of the invention, crude drug, may also Poria, Paeoniae Radix Rubra, Moutan Cortex and Cinnamomi Ramulus, may also Poria, Paeoniae Radix Rubra, Moutan Cortex, Cinnamomi Ramulus, Persicae Semen and radix et rhizoma glycyrrhizae, may also Poria, Paeoniae Radix Rubra, Salviae miltiorrhizae Radix et Rhizoma, Curcumae longae Rhizoma and Coptidis Rhizoma.

In the third aspect, the present invention provides a Chinese traditional medicine preparation for controlling the body weight and/or the blood fat, including thee traditional Chinese medicine composition and acceptable excipient in pharmacy of the first aspect of the invention.

In this paper, the term "pharmaceutically acceptable carrier" including excipient, pharmaceutically acceptable excipients, diluents, they are compatible with the active pharmaceutical ingredient. The use of a pharmaceutically acceptable excipient in preparing pharmaceutical preparations is known in general technique personnel of this field. The invention of pharmaceutical formulations comprising the composition the first aspect of the invention as active ingredients, mix the composition and the pharmaceutically acceptable carrier (such as ordinary technical personnel in the field known as excipients, diluents and flavoring agent) together, prepared into various preparations, preferably for solid and liquid preparations, such as tablets, pills, capsules (including sustained release or delayed release form), powder (such as dried powder), suspension, granule, tincture, syrup, emulsion, suspension, and the injection dosage forms such as sustained-release formulations. It is suitable for all kinds of dosage form, such as oral, parenteral, intravenous, mucosa, muscle, skin, eye, skin or skin after the dosage form is most preferably oral. In the specific embodiment of the third aspect, the preparation is powder preparation (preferably a frozen powder dry) or liquid preparation.

In the fourth aspect, the present invention provides a Chinese traditional medicine preparation for controlling the and/or body weight of the blood fat, the traditional Chinese medicine composition in the first aspect of the invention controls the blood fat and/or weight in dosage depending way.

In the fifth aspect, the traditional Chinese medicine composition in the first aspect can be applied in reducing the total cholesterol level, triacylglycerol level, and low density lipoprotein cholesterol level in the body; increasing body high density lipoprotein cholesterol level, reducing uric acid level, and/or reducing symptoms of fatty liver. The traditional Chinese medicine composition in the first aspect of the invention reduce body total cholesterol level, triacylglycerol level, low density lipoprotein cholesterol level, and/or increase high density lipoprotein cholesterol level in dosage depending way.

The invention has the beneficial effects that the Chinese medicine composition traditional of the invention can effectively control the body fat and/or body weight, especially be applied in reducing the total cholesterol level, triacylglycerol level, and low density lipoprotein cholesterol level in the body; increases body high density lipoprotein cholesterol level, reduce uric acid level, and/or reduce symptoms of fatty liver with a certain of difference. Therefore, it is easier to use these compositions for therapy; in addition, the preparation process of the traditional Chinese medicine composition can be used in the conventional process step by step, without new production equipment addition, it also has the advantages of simple steps, easy operation and monitoring, to further reduce the cost.

The present invention refers to publicly available documents, these documents are in order to better describe the invention, the contents of them are included in this invention. For easy understanding, the following will be specific examples to describe the invention in particular. These are just examples description, does not constitute a limit to the scope of this invention. For using the present invention, the invention can also get other technical solutions. According to the instructions, many changes of the invention is obvious to the technical staff in the field.

SPECIFIC IMPLEMENTATION MODALITIES

In the specific examples, the plant material (drug crude) and chemical reagents were purchased from the market channels of conventional materials.

The Preparation of Examples 1 ZL004

Take Poria 15 g, Paeoniae Radix Rubra 15 g, Moutan Cortex 15 g, and Cinnamomi Ramulus 15 g, After crushing, mix it and add 1000 mL pure water and soak it 1H, and then boil it in open container, then keep the evaporation stage and boil it with warm heat and simmer for 1 hour until the remaining liquid is about 200 mL, filter it and obtain 200 mL liquid medicine, freeze drying, to obtain the ZL004 drug 7G.

The Preparation of Examples 2 ZL005

Take Poria 15 g, Paeoniae Radix 15 g, Moutan Cortex 15 g, Cinnamomi Ramulus 15 g, and Persicae Semen 15 g, after crushing, mix it and add 1000 mL pure water and soak it 1H, and then boil it in open container, then keep the evaporation stage and boil it with warm heat and simmer for 1 hour until the remaining liquid is about 200 mL, filter it and obtain 200 mL liquid medicine, freeze drying, to obtain the ZL005 drug 9G. This method is same with the Guizhi Fuling pill.

The Preparation of Examples 3 ZL006

Take Poria 15 g, Paeoniae Radix Rubra 15 g, Moutan Cortex 15 g, Cinnamomi Ramulus 15 g, Persicae Semen 15 g, and radix et rhizoma glycyrrhizae 10 g, After crushing, mix it and add 1000 mL pure water and soak it 1H, and then boil it in open container, then keep the evaporation stage and boil it with warm heat and simmer for 1 hour until the remaining liquid is about 200 mL, filter it and obtain 200 mL liquid medicine, freeze drying, to obtain the ZL006 drug 11G.

The Preparation of Examples 4 ZL051

Take Poria 30 g, Paeoniae Radix-Rubra 30 g, Salviae miltiorrhizae Radix et Rhizoma 30 g, Curcumae longae Rhizoma 30 g, and Coptidis Rhizoma 12 g, After crushing, mix it and add 1000 mL pure water and soak it 1H, and then boil it in open container, then keep the evaporation stage and boil it with warm heat and simmer for 1 hour until the remaining liquid is about 200 mL, filter it and obtain 200 mL liquid medicine, freeze drying, to obtain the ZL051 drug 13G. This method is same with the Guizhi Fuling pill.

Examples 5 Study on the Effect of Drugs on Reducing Blood Lipid

Take the medicine ZL004, ZL005 and ZL006, 0.5% CMC-Na (carboxymethyl cellulose sodium) solution (25 mg/ml or 50 mg/ml); take atorvastatin as positive control drug (0.5% CMC-Na solution, 0.5 mg/ml), for the following experiment.

120 Wistar rats (male weight; 150 g; feeding environment: SPF grade animal room, free feeding, 12 h light/12 h dark) after adaptive breeding for one week, were randomly divided into normal control group (10 rats) and high-fat diet group (110 rats), and each rat was then numbered. The normal control group were fed with normal diet, high fat diet group were fed with high fat diet (78.8% basal diet (purchased from Beijing, Australia to feed Co. Ltd.) +1% cholesterol, +10% egg yolk powder, +10% lard, +0.2% sodium cholate), 30 days later, after determination, the hyperlipemia rats of high fat diet group were randomly divided into 10 groups (high fat model group, atorvastatin group (atorvastatin 5 mg/kg daily administration), ZL004 high dose group (daily administration of ZL004 500 mg/kg), ZL004 low dose group (daily administration of ZL004 250 g/kg), ZL005 high dose group (daily administration of ZL005 500 mg/kg), ZL005 low dose group (daily administration of ZL005 250 g/kg), ZL006 high dose group (daily administration of ZL006 500 mg/kg), ZL006 low dose group (daily administration of ZL006 250 g/kg), 10 rats in each group. The normal control group and high fat model group daily orally administered 0.5% CMC-Na solution, drug admonition group were orally administered with corresponding drugs administered continuously for 30 days to determine the levels of total cholesterol (TC), triacylglycerol (TG), high density lipoprotein cholesterol (HDL-C), low density lipoprotein cholesterol (LDL-C) and weight. No safety problems were found in the experiment.

The following experimental results are shown in the tables, the table 5.1 shows the effects of various drugs on the body weight of hyperlipidemia rats. Compared with normal control group, the weight of high fat model group were significantly increased, which is more obese; atorvastatin, each dose of ZL004 and ZL006 respectively reduced the body weight, close to or even lower than the normal control group; the obesity degree of each ZL005 groups were similar to the high fat model group.

TABLE 5.1 effects of drugs on weight body in rats with fat high ($\bar{x} \pm s$, n = 10)

| groups | dosage (mg/kg) | body weight (g) | body weight % (/high fat model group) |
|---|---|---|---|
| normal control group | — | 512.7 ± 43.8 | 89.48 ± 7.64 |
| high fat model group | — | 573.0 ± 78.7 | 100.00 ± 13.74 |
| Atorvastatin control group | 5 | 520.1 ± 52.8 | 90.77 ± 9.22 |
| ZL004 high dosage group | 500 | 515.6 ± 87.7 | 89.98 ± 15.29 |
| ZL004 low dosage group | 250 | 521.7 ± 47.2 | 91.04 ± 8.24 |
| ZL005 high dosage group | 500 | 536.9 ± 60.3 | 93.70 ± 10.52 |
| ZL005 low dosage group | 250 | 556.5 ± 89.2 | 97.13 ± 15.58 |
| ZL006 high dosage group | 500 | 495.9 ± 87.5 | 86.54 ± 15.26 |
| ZL006 low dosage group | 250 | 516.4 ± 46.8 | 90.12 ± 8.17 |

Table 5.2 shows the effects of various drugs on blood fat in hyperlipidemia rat model (with the average high fat model group is 100%). Compared with the normal control group, serum TC, TG, LDL-C of model group rats were significantly increased, while HDL-C decreased significantly; Atorvastatin and each doses of, ZL004 and ZL006 could significantly reduce rat serum TC, TG, LDL-C, Atorvastatin and each doses of ZL006, high dose ZL004 could significantly increase HDL-C; ZL005 showed little improvement effect on blood fat.

TABLE 5.2 effects of drugs on blood lipid level in fat high rats (compared with high fat model group, $\bar{x} \pm s$, n = 10)

| groups | dosage (mg/kg) | TC % (/model group) | TG % (/model group) | LDL-C % (/model group) | HDL-C % (/model group) |
|---|---|---|---|---|---|
| normal control group | — | 46.39 ± 12.39 | 57.61 ± 21.10 | 27.00 ± 10.58 | 164.29 ± 44.70 |
| high fat model group | — | 100.00 ± 16.00## | 100.00 ± 24.38## | 100.00 ± 17.98## | 100.00 ± 31.05## |
| Atorvastatin control group | 5 | 81.77 ± 14.65* | 70.50 ± 23.19* | 33.13 ± 11.62** | 178.57 ± 57.92** |
| ZL004 high dosage group | 500 | 84.23 ± 17.10* | 72.63 ± 30.21* | 70.84 ± 35.07* | 146.82 ± 47.15* |
| ZL004 low dosage group | 250 | 84.06 ± 16.58* | 71.19 ± 34.35* | 56.42 ± 32.50** | 138.25 ± 53.69 |
| ZL005 high dosage group | 500 | 98.52 ± 24.99 | 81.96 ± 36.53 | 79.54 ± 34.08 | 126.06 ± 39.68 |
| ZL005 low dosage group | 250 | 102.96 ± 30.53 | 73.61 ± 38.19 | 94.65 ± 35.43 | 123.40 ± 21.37 |
| ZL006 high dosage group | 500 | 75.52 ± 21.15* | 67.66 ± 27.63* | 58.89 ± 39.91** | 149.55 ± 53.18* |
| ZL006 low dosage group | 250 | 84.17 ± 16.01* | 71.19 ± 35.97 | 53.23 ± 15.90** | 136.45 ± 29.71* |

$p < 0.01$ compared with control group;
*$p < 0.05$ and
**$p < 0.01$, compared with model group Examples 6 Further Study on the Effect of Drugs on Lowering Blood Fat According to the test results, ZL005 was removed, ZL051 was introduced in the research; although there was no safety problem found, different dosage (especially low dosage) were involved in the research, in order to further investigate the effective dose of the drugs.

Take ZL004, ZL051 and ZL006 (0.5% CMC-Na solution, 7.5 mg/ml, 15 mg/ml, or 30 mg/ml), take atorvastatin as positive control drug (0.5% CMC-Na solution, 0.5 mg/ml), for the following experiment.

130 Wistar rats (male weight; 150 g; feeding environment: SPF grade animal room, free feeding, 12 h light/12 h dark) after adaptive breeding for one week, were randomly divided into normal control group (10 rats) and high-fat diet group (120 rats), and each rat was then numbered. The normal control group were fed with normal diet, high fat diet group were fed with high fat diet (78.8% basal diet (purchased from Beijing, Australia to feed Co. Ltd.)+1% cholesterol, +10% egg yolk powder, +10% lard, +0.2% sodium cholate), After 30 days, after determination, the hyperlipemia rats of high fat diet group were randomly divided into 10 groups (high fat model group, atorvastatin group (atorvastatin 5 mg/kg daily administration), ZL004 high dose group (daily administration of ZL004 300 mg/kg), ZL004 middle dose group (daily administration of ZL004 150 mg/kg), ZL004 low dose group (daily administration of ZL004 75 mg/kg), ZL051 high dose group (daily administration of ZL051 300 mg/kg), ZL051 middle dose group (daily administration of ZL051 150 mg/kg), ZL051 low dose group (daily administration of ZL051 75 mg/kg), ZL006 high dose group (daily administration of ZL006 300 mg/kg), ZL006 middle dose group (daily administration of ZL006 150 mg/kg), ZL006 low dose group (daily administration of ZL006 75 mg/kg), 10 rats in each group. The normal control group and high fat model group daily orally administered 0.5% CMC-Na solution, drug admonition group were orally administered with corresponding drugs administered continuously for 30 days to determine the levels of total cholesterol (TC), triacylglycerol (TG), high density lipoprotein cholesterol (HDL-C), low density lipoprotein cholesterol (LDL-C) and weight. No safety problems found in the experiment.

The following experimental results are shown in the tables, the Table 6.1 shows the effects of various drugs on the body weight of hyperlipidemia rats. Compared with normal control group, the body weight of high fat model group rats were significantly increased, which is more obese; atorvastatin, each dose of ZL004 and ZL006, high dose ZL051 respectively reduced the body weight, close to or even lower than the normal control group; the obesity degree of ZL051 low dose group and ZL051 middle dose group are close to high fat model group.

TABLE 6.1 effects of drugs on body weight of rats with high fat ($\bar{x} \pm s$, n = 10)

| groups | dosage (mg/kg) | body weight (g) | body weight % (/high fat model group) |
|---|---|---|---|
| normal control group | — | 471.7 ± 43.8 | 91.54 ± 8.51 |
| high fat model group | — | 515.3 ± 54.8 | 100.00 ± 10.64 |
| Atorvastatin control group | 5 | 465.7 ± 62.5 | 90.37 ± 12.13 |
| ZL004 low dosage group | 75 | 471.7 ± 46.6 | 91.53 ± 8.86 |
| ZL004 middle dosage group | 150 | 469.5 ± 94.3 | 91.11 ± 18.29 |
| ZL004 high dosage group | 300 | 446 ± 65.2 | 86.55 ± 12.65 |
| ZL051 low dosage group | 75 | 505.9 ± 52.7 | 98.18 ± 10.23 |
| ZL051 middle dosage group | 150 | 511.5 ± 77.7 | 99.26 ± 15.01 |
| ZL051 high dosage group | 300 | 574.1 ± 58.7 | 92.14 ± 11.39 |
| ZL006 low dosage group | 75 | 471.1 ± 41.4 | 91.42 ± 8.03 |
| ZL006 middle dosage group | 150 | 452.7 ± 64.4 | 87.85 ± 12.49 |
| ZL006 high dosage group | 300 | 465.4 ± 43.2 | 90.32 ± 8.38 |

Table 6.2 shows the effects of various drugs on blood fat in hyperlipidemia rat model (with the average high fat model group is 100%). Compared with the normal control group, serum TC, TG, LDL-C of model group rats were significantly increased, while HDL-C decreased significantly; Atorvastatin and middle/high doses of ZL004, ZL051, ZL006 could significantly reduce rat serum TC, TG, LDL-C, Atorvastatin and each doses of ZL004, middle/high doses of ZL051 and ZL006 could significantly increase HDL-C; low dose group of ZL004, ZL051 and Z006 showed little improvement effect on blood fat, indicated that the curative effect of these drugs were in a dose dependent manner.

TABLE 6.2 effects of drugs on blood fat of rats with high fat (compared with model group, $\bar{x} \pm s$, n = 10)

| Group | dosage (mg/kg) | TC % (/model group) | TG % (/model group) | LDL-C % (/model group) | HDL-C % (/model group) |
|---|---|---|---|---|---|
| normal control group | — | 50.26 ± 21.77 | 46.94 ± 9.18 | 35.84 ± 25.91 | 207.34 ± 39.29 |
| high fat model group | — | 100.00 ± 17.34## | 100.00 ± 32.47## | 100.00 ± 26.15## | 100.00 ± 40.76## |
| Atorvastatin control group | 5 | 77.03 ± 23.18* | 69.99 ± 17.21* | 67.93 ± 29.54* | 176.99 ± 37.57** |
| ZL004 low dosage group | 75 | 93.81 ± 24.74 | 75.94 ± 17.59 | 90.83 ± 28.35 | 145.56 ± 35.90* |
| ZL004 middle dosage group | 150 | 84.43 ± 17.86 | 72.88 ± 18.70* | 76.62 ± 23.26* | 156.55 ± 28.40** |
| ZL004 high dosage group | 300 | 78.29 ± 22.48* | 71.39 ± 10.26* | 69.64 ± 27.75* | 174.29 ± 34.96** |
| ZL051 low dosage group | 75 | 94.33 ± 23.52 | 83.46 ± 13.25 | 95.16 ± 27.01 | 121.06 ± 60.02 |
| ZL051 middle dosage group | 150 | 84.47 ± 10.02* | 78.47 ± 12.47 | 78.21 ± 10.44* | 150.66 ± 39.58* |
| ZL051 high dosage group | 300 | 77.81 ± 22.96* | 60.17 ± 13.88** | 70.56 ± 31.86* | 161.47 ± 19.90** |
| ZL006 low dosage group | 75 | 84.33 ± 16.07 | 77.82 ± 10.93 | 91.31 ± 20.33 | 128.15 ± 28.39 |
| ZL006 middle dosage group | 150 | 69.75 ± 18.35** | 58.80 ± 14.02** | 72.46 ± 27.82* | 152.83 ± 36.81** |
| ZL006 high dosage group | 300 | 75.30 ± 20.54** | 55.71 ± 22.19** | 71.34 ± 30.24* | 171.11 ± 23.25** |

$p < 0.01$ compared with control group;
*$p < 0.05$ and
**$p < 0.01$, compared with model group Examples 7 Clinical Trials After informed consent, hyperlipidemia volunteers were oral administered with drug which was prepared according to example 1 and example 3, the preparation process including boiling, concentrated and filtered without freeze drying volunteers toke drug twice a day, each time 100 mL liquor (daily dose equivalent to the initial 1000 mL content and corresponding proportion of crude drug), last for 30 or 60 days.

Before and after treatment, the body weight and serum index of each volunteers were shown in the tables, the Table 7.1 showed the weight and serum indexes of one volunteers who toke liquid prepared following example 1 protocol, before and after the drug administration for 30 days, the weight, TC, TG, LDL and HDL were well improved.

TABLE 7.1 comparison of weight and serum index before and after
toke liquid prepared following example 1 protocol

| Sex/Age | state | body weight (Kg) | TC (mg/DL) | TG (mg/DL) | LDL (mg/DL) | HDL (mg/DL) |
|---|---|---|---|---|---|---|
| M/44 | before dose | 71.3 | 224 | 216 | 131 | 50 |
|  | after dose | 65.8 | 191 | 190 | 120 | 55 |

Table 7.2 showed the weight and serum indexes of 3 volunteers who toke liquid prepared following example 3 protocol, before and after the drug administration for 30 days, the weight, TC, TG, LDL, HDL and uric acid were well improved.

TABLE 7.2 comparison of weight and serum index before and after
toke liquid prepared following example 3 protocol

| Sex/Age | state | body weight(Kg) | TC (μmol/DL) | TG (μmol/DL) | LDL (μmol/DL) | HDL (μmol/DL) | uric acid (μmol/DL) |
|---|---|---|---|---|---|---|---|
| M/51 | before dose | 65.8 | 6.35 | 2.07 | 3.72 | 1.26 | 471 |
|  | after dose | 62.5 | 5.05 | 1.20 | 3.05 | 1.52 | 402 |
| M/53 | before dose | 65.4 | 5.75 | 1.71 | 3.59 | 1.15 | 513 |
|  | after dose | 62.5 | 4.91 | 1.48 | 2.71 | 1.47 | 428 |
| F/56 | before dose | 70.7 | 5.63 | 1.25 | 3.31 | 1.13 | 582 |
|  | after dose | 63.2 | 4.82 | 1.14 | 2.69 | 1.45 | 378 |

Table 7.3 showed the weight and serum indexes of 4 volunteers who toke liquid prepared following example 1 protocol, before and after taking the liquid for 30 days, weight, TC, TG, LDL, HDL, uric acid and fatty liver etc. were improved.

TABLE 7.3 comparison of weight and serum index before and after
toke liquid prepared following example 1 protocol

| Sex/Age | state | body weight(Kg) | TC (μmol/DL) | TG (μmol/DL) | LDL (μmol/DL) | HDL (μmol/DL) | uric acid μmol/(DL) | fatty liver symptom |
|---|---|---|---|---|---|---|---|---|
| M/55 | before dose | 64.6 | 6.32 | 8.08 | 3.22 | 1.26 | 463 | + |
|  | after dose | 61.3 | 5.06 | 1.73 | 2.56 | 1.52 | 415 | — |
| M/56 | before dose | 73.4 | 6.04 | 1.71 | 3.26 | 1.21 | 438 | +++ |
|  | after dose | 65.8 | 5.03 | 1.26 | 2.55 | 1.51 | 412 | — |

"+"light fatty liver,
"+++"severe fatty liver,
"—"no fatty liver.

The invention claimed is:

1. A traditional Chinese medicine composition for control blood fat and/or body weight, consisting of Poria for 3 parts approximately, Paeoniae Radix Rubra for 3 parts approximately and at least one crude drug group selected from the group consisting of:
   Group A: Moutan Cortex for 3 parts approximately and Cinnamomi Ramulus for 3 parts approximately;
   Group B: Moutan Cortex for 3 parts approximately, Cinnamomi Ramulus for 3 parts approximately, and Glycyrrhizae Radix et Rhizoma for 2 parts approximately; and,
   Group C: Salviae miltiorrhizae Radix et Rhizoma for 3 parts approximately, Curcumae longae Rhizoma for 3 parts approximately and Coptidis Rhizoma for 1.2 parts approximately.

2. The traditional Chinese medicine composition of claim 1 wherein the preparation is powder.

3. The tradition Chinese medicine composition of claim 2, wherein the powder is lyophilized powder.

4. The traditional Chinese medicine composition of claim 1, wherein the preparation is liquid.

5. The composition of claim 1, wherein the at least one crude drug group is selected from the group consisting of: Group A; and Group C.

6. A method for preparing the traditional Chinese medicine composition specified in claim 1, wherein a preparation process includes adding water and/or alcohol decoction.

7. The method of claim 6, further comprising:
   (1) crush and mix the crude drug, and obtain mixed powder of the crude drug;
   (2) add water into and soak the mixed powder of crude drug obtained in step (1), then perform decoction in an open container, and obtain the decocted liquid;
   (3) filter the decocted liquid obtained in step (2), and obtain a medicine liquid; and,
   (4) dry the medicine liquid obtained in step (3).

8. The method of claim 6, wherein the adding and/or alcohol decoction step is carried out in an open container.

9. The method of claim 7, wherein step (2) comprises soaking for 0.5-2 hours and decoction for 0.5-2 hours.

10. The method of claim 7, wherein the drying step of step (4) is freeze drying.

11. A method for reducing total cholesterol level, triacylglycerol level, and low density lipoprotein cholesterol level in body, and increasing body high density lipoprotein cholesterol level, reducing body uric acid level, and/or reducing symptoms of fatty liver, comprising administering the composition of claim 1 to a subject in need thereof.

* * * * *